United States Patent [19]
Goldman

[11] Patent Number: 5,751,911
[45] Date of Patent: May 12, 1998

[54] REAL-TIME WAVEFORM ANALYSIS USING ARTIFICIAL NEURAL NETWORKS

[76] Inventor: Julian M. Goldman, 130 S. Hudson St., Denver, Colo. 80222

[21] Appl. No.: 747,460

[22] Filed: Nov. 12, 1996

Related U.S. Application Data

[62] Division of Ser. No. 779,219, Oct. 18, 1991, Pat. No. 5,598,508.

[51] Int. Cl.$^6$ .......................... G06F 15/48; G06F 15/18
[52] U.S. Cl. .................. 395/22; 395/20; 395/21; 395/23
[58] Field of Search ................ 395/22, 23, 20, 395/21

[56] References Cited

U.S. PATENT DOCUMENTS

| | | | |
|---|---|---|---|
| 4,972,473 | 11/1990 | Ejiri et al. | 395/22 |
| 5,092,343 | 3/1992 | Spitzer et al. | 395/22 |
| 5,093,792 | 3/1992 | Taki et al. | 395/22 |
| 5,119,468 | 6/1992 | Owens | 395/22 |
| 5,121,443 | 6/1992 | Tomlinson | 395/22 |
| 5,150,323 | 9/1992 | Castelaz | 395/24 |
| 5,181,171 | 1/1993 | McCormack et al. | 395/22 |

Primary Examiner—George B. Davis
Attorney, Agent, or Firm—Baker, Maxham, Jester & Meador

[57] ABSTRACT

A real-time waveform analysis system utilizes neural networks to perform various stages of the analysis. The signal containing the waveform is first stored in a buffer and the buffer contents transmitted to a first and second neural network which have been previously trained to recognize the start point and the end point of the waveform respectively. A third neural network receives the signal occurring between the start and end points and classifies that waveform as comprising either an incomplete waveform, a normal waveform or one of a variety of predetermined characteristic classifications. Ambiguities in the output of the third neural network are arbitrated by a fourth neural network which may be given additional information which serves to resolve these ambiguities. In accordance with the preferred embodiment, the present invention is applied to a system analyzing respiratory waveforms of a patient undergoing anesthesia and the classifications of the waveform correspond to normal or various categories of abnormal features functioning in the respiratory signal. The system performs the analysis rapidly enough to be used in real-time systems and can be operated with relatively low cost hardware and with minimal software development required.

13 Claims, 6 Drawing Sheets

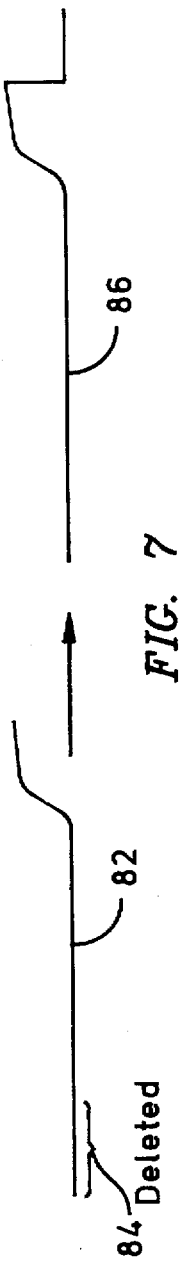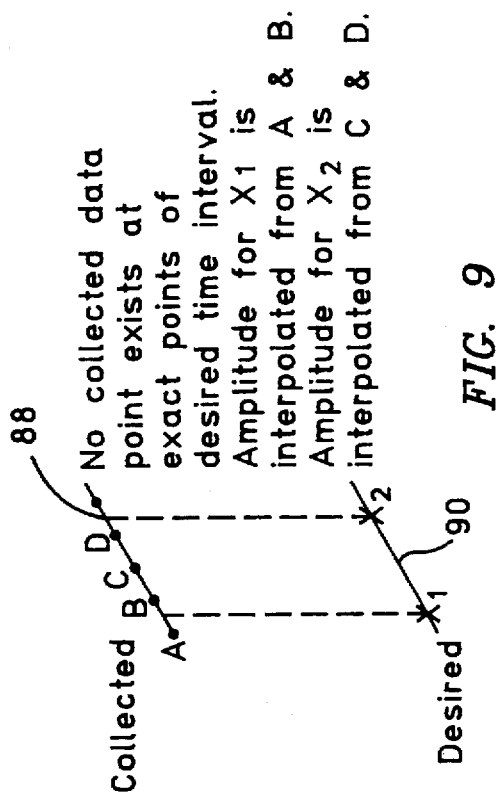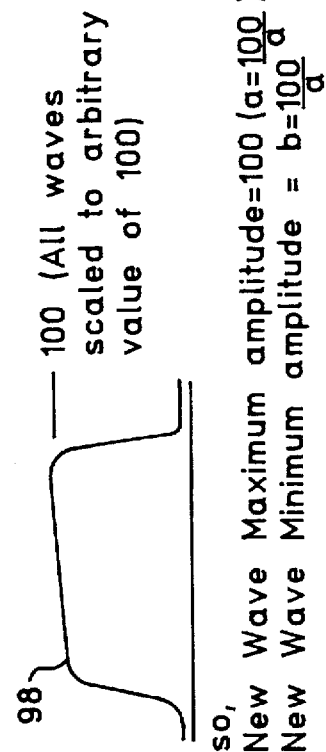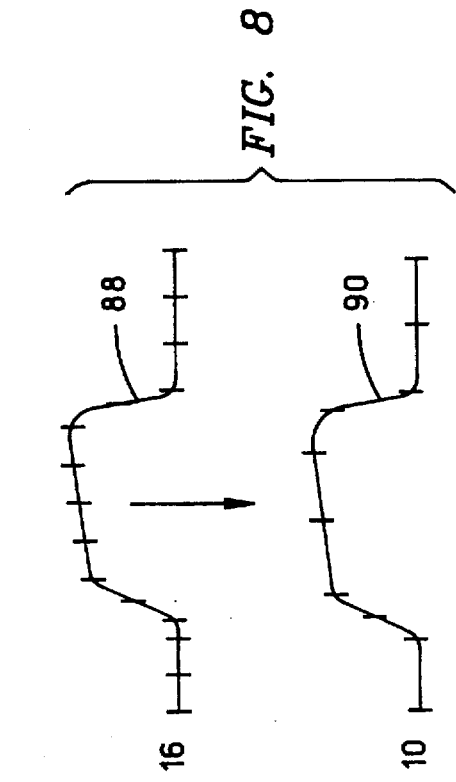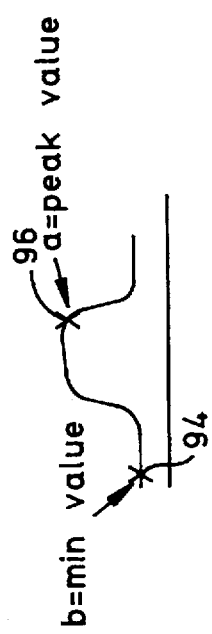
FIG. 7
FIG. 8
FIG. 9
FIG. 10
FIG. 11

| Output Node | Class | Description |
|---|---|---|
| 1 | Partial Wave | Incomplete waveform. Bad selection. |
| 2 | Normal | Normal Capnogram. |
| 3 | Cleft in Plateau | Patient breathing against the ventilator |
| 4 | Inspiratory Valve | Leaking inspiratory valve. |
| 5 | Expiratory Valve | Leaking expiratory valve. |
| 6 | Steep Plateau | Abnormally Steep Plateau. |

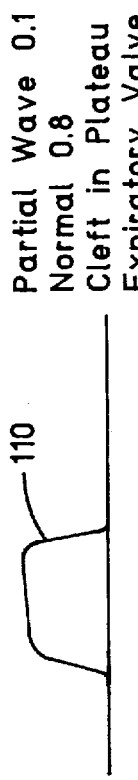

FIG. 18

Partial 0.0
Normal 0.6
Cleft 0.1
Exp Valve 0.5

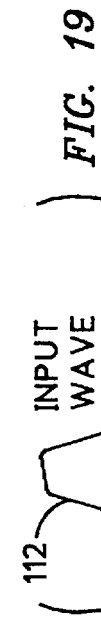

FIG. 19

Partial Wave 0.1
Normal 0.8
Cleft in Plateau 0.2
Expiratory Valve Defect 0.0

| Output Node | Class |
|---|---|
| 1 | Normal |
| 2 | Cleft in Plateau |
| 3 | Inspiratory Valve |
| 4 | Expiratory Valve |
| 5 | Unknown |

REAL-TIME WAVEFORM ANALYSIS USING ARTIFICIAL NEURAL NETWORKS

This application is a division of application Ser. No. 07/779,219, filed Oct. 18, 1991, U.S. Pat. No. 5,598,508.

BACKGROUND OF THE INVENTION

1. Technical Field

This invention relates to waveform analysis and more particularly to a system for performing real-time waveform analysis using artificial neural networks.

2. Discussion

Accurate waveform analysis plays a crucial role in many fields. That is, many technical areas involve problems in analyzing an incoming signal having a characteristic waveform which must be interpreted and classified. Some examples of such signals include the analysis of audio, sonar, and electromagnetic waves from various sources. For example, detailed analysis and classification of speech signals is required to perform automated speech recognition. Another example occurs in analysis of seismographic signals. Numerous waveform analysis applications exist in the medical field. Examples of physiologic waveforms which are subject to analysis include respiratory wave analysis including pressure and gas concentrations, vascular pressure waves (arterial, etc.), airway pressure waves; electrocardiograms; electroencephalograms; pressure wave analysis in a cardiopulmonary bypass machine circuit, plethysmograms and bioimpedance waves.

Some of the more difficult tasks involved in analyzing such signals include front end (preprocessing) steps, including waveform segmentation; classification of waveforms into predetermined classes; and interpreting of ambiguous data such as ambiguous classification results. Difficulties in performing tasks such as these are compounded because of wide variations in such waveforms due to countless factors causing the signal to deviate in frequency, amplitude, shape, etc. from expected norms. Because of these variations, the task of developing algorithms and writing software to automatically perform waveform analysis frequently becomes a daunting, monumental task. This "software bottleneck" has slowed the development of systems in this area. Even when large sums of time and money are spent to develop such software algorithms, results in many areas are still not satisfactory.

A further problem with conventional approaches is that they are frequently computationally expensive which either necessitates enormous computing power, or simply precludes their use in systems which must perform in real-time. For example, in the analysis of physiological waveforms, real time performance is often essential to achieve results fast enough to take corrective responses to abnormalities in a patient's physiological functioning.

A promising alternative to conventional symbolic sequential computing techniques is offered by artificial neural network systems. Neural network architectures, which are loosely based on knowledge of the neuroanatomy of the brain, have been shown to perform well at tasks such as classification of waveforms having subtle differences—tasks which heretofore have been limited to performance by humans. In addition to their robust ability to recognize characteristic waveforms which vary widely from predicted shapes, neural networks also promise to offer a solution to the "software bottleneck" discussed above. This is because explicit algorithms need not be developed for neural networks to recognize waveforms. Instead, these systems, trained with exemplars, they converge to an acceptable solution. In addition, once trained, a neural network can generally perform a recognition task rapidly due to its inherent parallelism. See R. P. Lippmann "An Introduction to Computing with Neural Networks" IEEE ASSP Magazine, April 1987, page 4 for a discussion of the better-known neural network architectures and techniques. Despite the promising outlook, many difficult remain to be solved in such areas as preprocessing data to make it suitable for processing by the neural network, optimizing the architectures and learning paradigms for the recognition process, as well as postprocessing and interpretation of ambiguous results.

Thus it would be desirable to provide a system and method to perform waveform analysis which overcomes some or all of these shortcomings. It would be desirable to have a system which can perform accurate analysis and classification of waveforms without requiring extensive algorithm and software development time. Further, it would be desirable to provide such a system which can perform waveform analysis in real-time with readily available and reasonably priced hardware. It would further be desirable to provide a waveform analysis system which can readily analyze and classify waveforms which deviate substantially from predicted patterns. Further, it would be desirable to provide a waveform analysis system which makes use of the advantages of neural network architectures and also resolves inherent preprocessing, analysis and postprocessing difficulties.

SUMMARY OF THE INVENTION

Pursuant to the present invention, a method of analyzing waveforms having characteristic features in a signal using neural networks is provided. Initially, a first portion of the signal is transmitted to a neural network so that AN consecutive samples of said signal are transmitted to N input nodes of the neural network, so that the transfer causes the neural network nodes to receive data from buffer locations having the same index number. An output is then generated by the neural network which is a representation of the index number of the input node receiving the starting point of the waveform, since the neural network has been previously trained to recognize starting and end points of the characteristic waveforms respectively. In accordance with another aspect of the present invention, a third neural network then receives the contents of the buffer between the identified starting points and ending points. This neural network has been trained to produce an output which serves to classify the waveforms. In accordance with another aspect of the present invention, a fourth neural network is then trained to resolve any ambiguities in the third neural network output using additional information.

In accordance with another aspect of the present invention, a system is provided for analyzing a characteristic waveform in a signal using neural networks in the manner described above.

BRIEF DESCRIPTION OF THE DRAWINGS

The various advantages of the present invention will become apparent to one skilled in the art by reading the following specification and by reference to the following drawings in which:

FIG. 7 is a diagram illustrating a technique for insuring that sufficient lead and lag portions of a waveform are sampled;

FIG. 8 is a diagram illustrating the time normalization of a waveform;

FIG. 9 is a diagram illustrating additional details of the time normalization shown in FIG. 8;

FIG. 10 is an illustration of the amplitude normalization process in accordance with the present invention;

FIG. 11 is an illustration of additional details of the amplitude normalization process;

FIG. 17 illustrates the output classifications produced by neural network 3 in accordance with the present invention;

FIG. 18 is an example of the output of neural network 3 for an exemplary waveform;

FIG. 19 is an example of an ambiguous output from neural network 3 requiring arbitration;

FIG. 20 is a table of the outputs of neural network 4 for performing arbitration.

DESCRIPTION OF THE PREFERRED EMBODIMENTS

The present invention provides the system and method for analyzing waveforms which may originate in numerous applications as discussed above. To illustrate the use of the techniques of the present invention, a non-limiting example will be described in accordance with a preferred embodiment involving physiologic respiratory signals. In particular, the preferred embodiment involves analysis of capnograms, which are measurements of carbon dioxide concentration in inhaled and exhaled breath during respiration over time. The carbon dioxide concentration measurement is usually performed by a measurement of absorption of infrared light in a sample of a subjects exhaled breath, although other techniques such as mass spectroscopy can also be used to measure CO2 concentration.

The goal when analyzing physiologic signals such as capnograms, (as well as many other types of waveforms) is to locate and separate each event in a time series of data for a subsequent pattern identification. In the capnogram, the event of interest is the portion of the signal produced during expiration. Once each individual event is isolated by the system, it is then analyzed by the pattern recognition portion of the system and a diagnosis is displayed. A pattern classification of each individual capnogram permits the diagnosis of normal and various abnormal capnograms.

Figure 1:
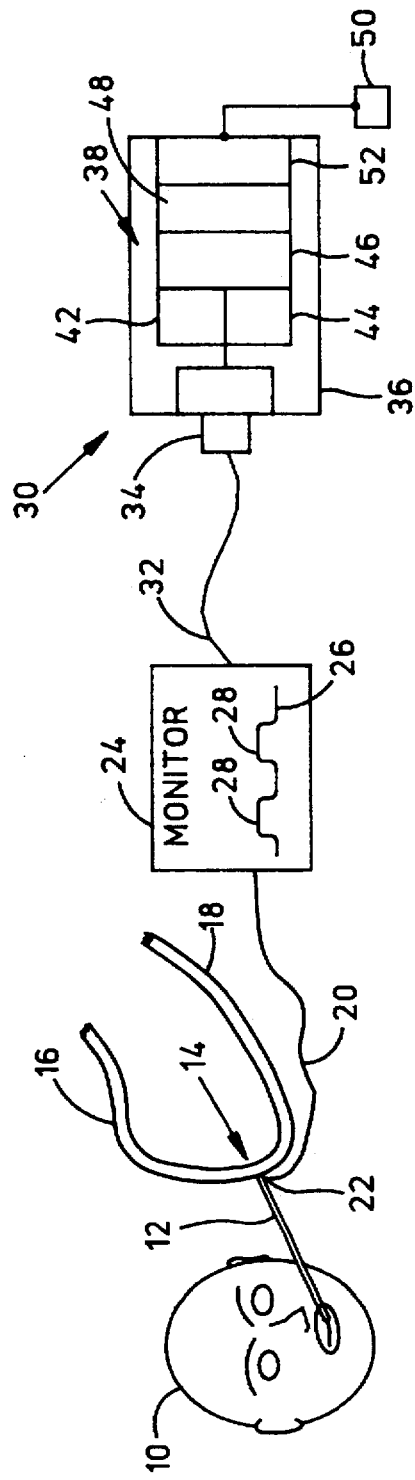
FIG. 1 is a diagram of the main components of a preferred embodiment of the present invention for use in automated capnogram waveform analysis.

Referring now to FIG. 1, the main components of the preferred embodiment of the present invention are shown. A subject or patient 10 undergoing anesthesia has a breathing tube 12 (endotracheal tube) inserted into his trachea. The breathing tube is connected to an anesthesia machine and breathing circuit 14 in a conventional manner which is connected to an inspiratory valve (not shown) in the intake 16 segment of the tube and an expiratory valve (not shown) connected to the expiratory portion 18 of the breathing circuit 14. In operation, a bellows (not shown) will force air into the subject's lungs through the breathing tube 12 and the subject will exhale unassisted forcing CO2-rich gas to pass out of the breathing tube 12 and into the expiratory portion of the breathing circuit 18. A gas sampling catheter 20 is attached to the breathing tube 12 at point 22. The gas sampling catheter is fed to a respiratory gas monitor which may comprise an Ohmeda Model 5250 respiratory gas monitor manufactured by Ohmeda Corporation of Louiseville, Colo. The respiratory gas monitor 24 analyzes the CO2 content of the gas in the sampling catheter 20 and produces a capnogram signal 26 which contains characteristic waveforms 28 which represent elevated CO2 levels during expiration.

Ordinarily, the capnogram signal 26 is monitored by operating room personnel to insure that a normal signal is present. Various kinds of abnormalities in the capnogram are indicative of a variety of abnormal conditions and will generally require immediate corrective action. While some automatic waveform analysis techniques have been employed previously to detect such abnormalities, the performance of such systems has had several drawbacks limiting their usefulness as discussed above.

In accordance with the present invention, the capnogram 26 is analyzed using an artificial neural network-based system to perform preprocessing, classification, and post-processing of individual capnograms. In more detail, the waveform analysis system 30 of the present invention employs an input line 32 which carries an analog capnogram signal 26. This analog signal is converted to a digital signal by an analog to digital converter 34 which may comprise a Model DASH-16F analog to digital converter manufactured by Metrabyte Corporation of Taunton, Mass. This analog to digital converter 34 includes direct memory access (DMA) control and is used to convert and store the CO2 capnograph signal 32 into computer memory without using CPU time.

In particular, the analog to digital converter 34 output is fed to a host computer 36 which, for example, may comprise a PC computer employing a 486, 33 megahertz chip. The analog to digital conversion is performed at 20 hertz which is sufficiently fast to capture all the features of the capnogram 26 with a minimum amount superfluous data. A waveform analysis program 38 in accordance with the present invention is stored in the PC 36 memory and performs the steps of waveform analysis as described hereinafter.

In particular, a memory storage area in the program 36 comprises a circular input buffer 40 which temporarily stores the capnogram signal 26 before transferring it to a pair of neural networks, designated neural network No. 1, 42 and neural network No. 2, 44. These neural networks are trained to locate the start point and end point of an individual capnogram 28. Once the start point and end point are defined by neural network No. 1, 42 and No. 2, 44 outputs, the capnogram waveform 28 defined by these points is transmitted to neural network No. 3, 46 which has been trained to recognize specific abnormal waveform features. For example, referring now to FIG. 2, a normal capnogram 54 is shown along with a capnogram 56 illustrating an inspiratory valve defect, and one having a cleft in the plateau 58 and another capnogram 60 indicating an expiratory valve defect having an elevated base line. The present invention thus is able to recognize these and other characteristic waveform shapes automatically in real-time to permit corrective action to be taken.

In cases where neural network 346 produces an output which is ambiguous, that is, not clearly one category or another, neural network No. 48 is used to perform arbitration using additional information about the physiologic state of the patient 10 to account for atypical waveforms. The output of neural network No. 48 is a representation of the classification of the normal or abnormal waveform 28 which may then be displayed in various ways by a display unit 50. For example, abnormal waveforms may trigger an alarm to alert operating room personnel to the condition, or may further be processed by subsequent systems which may then specify corrective measures to be taken.

The software 38 contains control logic 52 which directs the flow and decisions of the program as discussed in more detail below.

In more detail, the circular input buffer 40 is over-sized so that about two minutes of data can be stored. Nevertheless, the goal of the preferred embodiment is to be able to recognize a capnogram 28 observation in 15 seconds or less. Data is sampled at 20 hertz and fed to neural networks one and two, each having 300 input nodes. Thus, since there is a one to one correspondence of collected data points to input nodes a maximum of 300 data points or (300+20) equals 15 seconds can be analyzed. A given location in the buffer 40 is defined as an index point.

Figure 3:
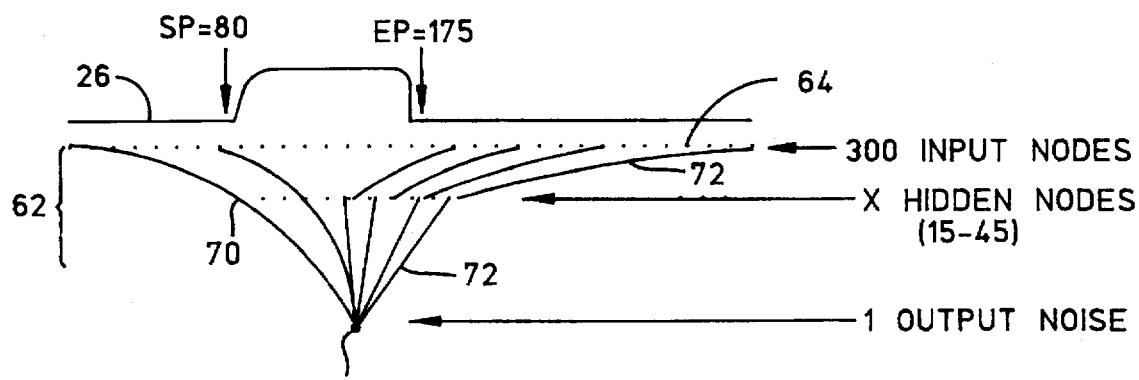
FIG. 3 is a diagram of a neural network configured to produce an output which identifies the waveform's starting point or end point.

Referring now to FIG. 3 a representation of a neural network 62 having 300 input nodes 64 and one output node 66 is shown. Each of the 300 input nodes receive data from the capnogram signal 26 contained in the input buffer 40 where data in each corresponding index number in the buffer is transmitted to one of the 300 input nodes having a corresponding index number. It will be appreciated by those skilled in the art that neural network 62 may comprise a conventional three-layer back-prop neural network having 300 input hidden nodes 70 which may optimally include 15 to 45 hidden nodes and synaptic connections 72 between each node in neighboring layers. That is, in accordance with conventional multilayer perceptron, each node 64 is connected to each hidden node 70 and likewise each hidden node 70 is connected to the output node 66.

Further details of multilayer perceptrons may be found in the above referenced paper by Lippmann, entitled "Introduction to Computing Using Neural Network". In addition, a software package sold by Ward Systems Group of Frederick, Md. known as NeuroShell is available to implement neural networks 1–4 in software in accordance with the present invention. Further, a code generation module available from Ward Systems Group facilitates in development of the control logic for controlling the over all system. Further, a hardware training board available from NeuroShell may be advantageously employed in permitting rapid training of the neural networks as described below. Alternatively, it will be appreciated that the neural networks may be implemented in hardware using, for example, a neural network chip such as the ETANN chips manufactured by Intel. Corp. of Sunnyvale, Calif.

Figure 4:
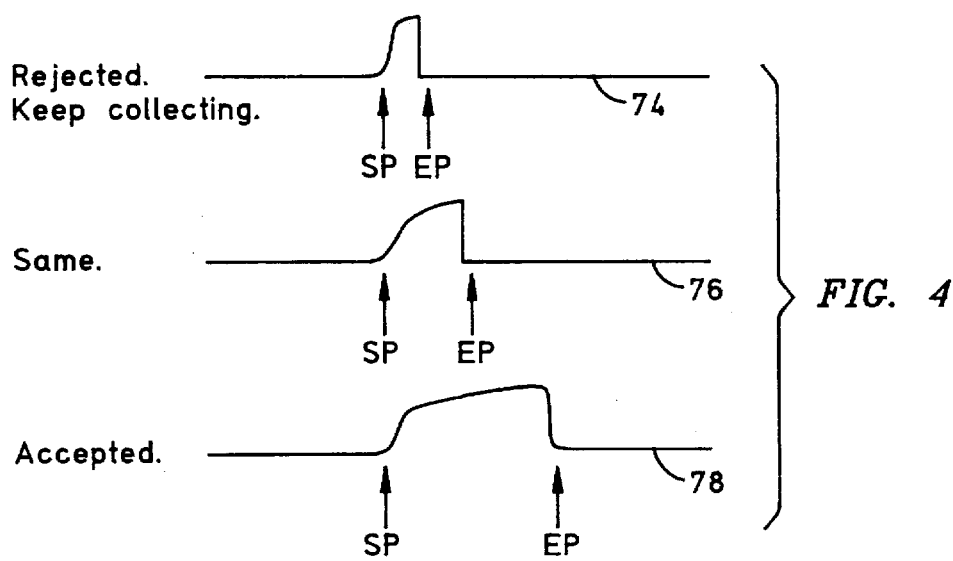
FIG. 4 is a diagram showing the progression of a signal containing a waveform into the input buffer of the present invention.

Returning to FIG. 3, while the input signal 26 is shown as filling all 300 index points, in practice, it is not desirable to wait 15 seconds in order to fill the data buffer with 300 points before analysis is performed. This is because if a given wave was, for example, 10 seconds long, 5 seconds would be wasted for the buffer to fill and little time would be left to complete the analysis before another wave was generated. Thus, it is desirable to analyze a partially filled buffer. As shown in FIG. 4 the buffer is filled gradually until a complete waveform has been received. Thus, the first waveform 74 in FIG. 4 is rejected because it is not complete, likewise the waveform 76 is rejected and finally waveform 78 is accepted by the system. This is accomplished as follows.

Figure 5:
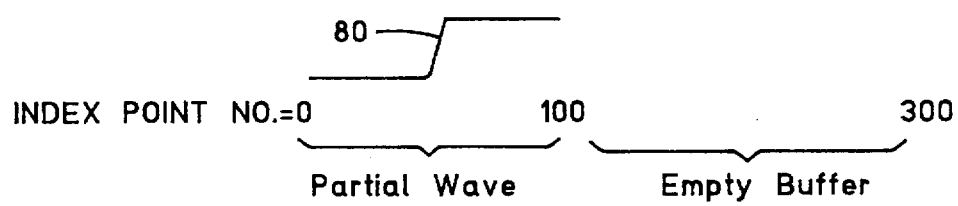
FIG. 5 is a diagram illustrating a sampling of a signal containing a partial waveform.
Figure 6:
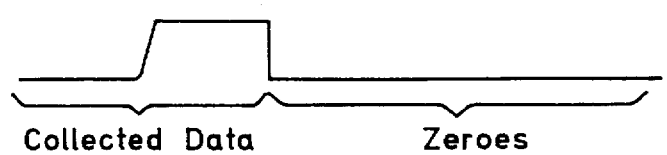
FIG. 6 is a diagram illustrating the setting of buffer value to 0 for incomplete waveforms.

Referring to FIG. 5, a waveform 80 is shown after part of the wave has been collected. It should be noted that index point 0 would contain the digitized value of the amplitude of the waveform (capnogram) at time 0. Index point 20 would contain the value measured 20 points (1 second) later. Initially, a few, five for example, data points are collected and sent to neural networks 1 and 2. The neural networks 1 and 2 would receive 300 numbers from the buffer. Since some signal must be passed to the input nodes of these neural networks, the empty buffer locations, which were assigned values of −1, are given the value of zero for analysis. Thus, the first five data points would contain actual wave amplitude values and the remaining 295 input nodes would be 0. As shown in FIG. 5 sometime later the waveform amplitude values contained in 100 index points of wave 80 are transmitted to neural networks 1 and 2 and the remaining 200 points are empty places from the buffer which are padded with zeros before transfer to the network as illustrated in FIG. 6.

Each time data is transmitted to neural network 1 or 2, output node 66, shown in FIG. 3, will produce an output which in the case of neural network 1 will represent the index number of the starting point of the wave; in the case of neural network 2, output node 66 will assume a state having a numerical value representing the index number of the end point of the wave. For example, as shown in FIG. 3 the starting point occurs at index point 80 in the buffer as well as input node 80 in neural network 1. This will cause the neural network 62 to produce a value at output node 66 of 80. Likewise, in the case of neural network 2, since the end point occurs at index point 175 the output node will produce a value of 175. It will be appreciated that by training neural networks 1 and 2, in accordance with conventional back prop techniques, using training sets of input data similar to conventional capnograms, the weights of synaptic connection 72 will converge to solution producing output values in the output node 66 corresponding to the index number of the wave starting point or ending point. Also, using two different neural networks permits independent training and testing sets, and a different number of hidden nodes for each network. It will also be appreciated that neural networks 1 and 2 could be combined into a single network having two output nodes, one designating the starting point and one output node designating the end point. However, it has been found that a number of advantages are achieved by separating this function into two separate neural networks as illustrated herein.

Referring again to FIG. 6, it will be appreciated that at this stage a correct starting point may be identified by neural network 1 but that index point 100, for example, will incorrectly be identified by neural network 2 as an ending point. In order to recognize that this is not a valid end point, the present invention compares the index of the end point determined by neural network 2 with the index of the last collected real data point. Real data must exist at the end point index for the wave to be considered captured. Thus, referring again to FIG. 4 the end point identified by neural network 2 will be rejected in the case of the waveform at stages 74 and 76, but will finally be accepted at stage 78. Thus, by repeatedly sampling data to determine the location of the end of the waveform it is not necessary to wait for a buffer to fill before passing its contents to the neural networks 1 and 2 for analysis. Also, it will be appreciated that the use of the analog to digital converter with direct memory access hardware permits data to continue being collected into the buffer in a background process while neural networks 1 and 2 attempt to locate the starting point and end point.

Another situation which must be accounted for occurs if the waves are arriving at a relatively low frequency, and the buffer is partially filled with zeros waiting for a wave to begin. This situation is illustrated in the curve 82 shown in FIG. 7. If this happens, the end point determined by neural network 2 will never fall after the last collected data point. For example, they both may be at data point 300. Further, any time the end point is found in the last 20 nodes, it will be desirable to collect additional data. This will permit neural network 2 to get a good look at the terminal portion of the wave. To handle both these situations, the earliest 20 points 84 are deleted from the buffer so that the wave is "slid" to the left to make room for additional data collection. Deletion is performed by moving the 0 index value 20 points later, (to the right), and changing the 20 data point valves to −1. This will result in the wave 86 shown in FIG. 7. The assumption is that if no valid end point has yet been identified, (or if it found in the last 20 nodes), it is unlikely that the earliest data points are part of a valid wave and can be removed. Note that the number of neural network input points was chosen to be significantly larger than the anticipated maximum wave duration. Further, this shifting procedure insures that neural network 3 will have sufficient information about the terminal portion of the wave to make accurate classifications. This is because it is desired that neural network 3 use as much information about the waveform including the lead and lag portion for recognizing and classifying waveforms, in much the same way that a human observer would use this information to recognize characteristic waveforms.

The software control program 52 continues in the above described fashion—collecting a few data points, sending them to neural networks 1 and 2, and analyzing the outputs of the neural networks—until both start and end points are plausible. Once this happens, the contents of the buffer between the start and end points is extracted and sent to neural network 3 for pattern recognition. The buffer will continue to collect new data so that no waves are missed. That is, subsequent processing is performed at a rate considerably faster than the rate at which new data enters the buffer. This is an important consideration which permits the present invention to be utilized in real-time.

Once neural networks 1 and 2 locate valid start and end points of the wave, the values of the amplitude of the wave between the start and end points are sent to neural network 3. If further analysis (discussed below) by neural network 3 confirms that we have a valid wave, the buffer will be cleared almost up to the end point index. As mentioned above, the buffer is cleared up to about 5 points earlier than the end point. Thus, when newly collected data is analyzed a few old data points are presented to neural networks 1 and 2 along with the new data. This technique increases the likelihood that neural network 1 will see enough of the starting region of the wave to identify it. This technique underscores an important principle of the present invention. That is, to try to mimic the way a human would identify starting points and end points. A human must see a bit of the wave before the start point and after the end point to be certain that those points are valid.

Figure 2:
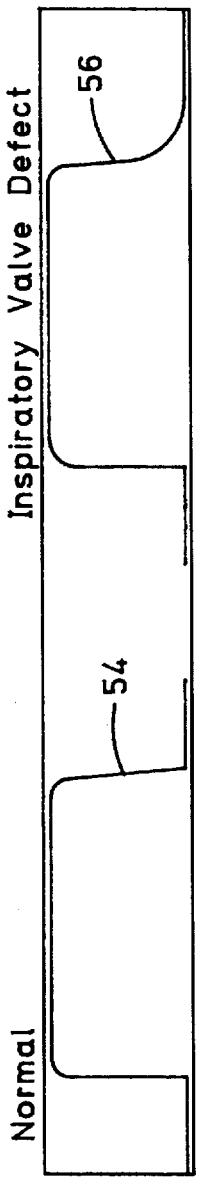
FIG. 2 is a diagram showing normal and abnormal capnogram waveforms to be identified by the present invention.

Neural network 3, 46 is a three layer perceptron having 50 number of input nodes, so that it is sufficiently wide to accept the expected waves between start points and end points. In accordance with the preferred embodiment, neural network 3 has an output corresponding to each unique classification, such as the classifications 54–60 shown in FIG. 2. Thus, if a normal wave such as wave 54 in FIG. 2 is presented to neural network 3, the output corresponding to normal should be 1.0 and the outputs corresponding to the other classes of abnormal waves should all be zero or close to it.

However, before presentation to neural network 3 the wave must be normalized or scaled. This insures that all waves have an arbitrary maximum value of 100 and approximately the same length of lead and lag segments. This step facilitates identification by neural network 3 because it reduces the wide variation in amplitude and duration that such waves can have. For example, a wave of amplitude 6 and duration 9, and a wave of amplitude 4 and duration 8 may both be completely normal and recognized as such based on their shape. There are a number of ways to normalize this data. These may be summarized as follows:

1. Time normalization—this technique is necessary when n data points must be mapped to x input nodes.

2. Amplitude normalization—this is used to emphasize certain morphologic features (and de-emphasize others) to improve network performance and efficiency.

3. Lead and lag normalization—this refers to aligning the rising and falling segments of each wave with respect to the input nodes of neural network 3, in order to reduce the translational variability of the input vector.

Time normalization is used to calculate the inputs to neural network 3. The time series of data delineated in the buffer by the start point and end point consists of a variable number of data points (analog-digital samples.) This time series must be expanded or reduced in time so that it may be mapped to the 50 input nodes of neural network 3. The process by which the data is arranged into 50 equally spaced points is as follows: each new data point is calculated by finding the two original data points which most closely approximate the desired data point in time. Then, the amplitude of the wave corresponding to the desired point in time is calculated by literally interpolating between those two nearest original data points. For example, referring to FIGS. 8 and 9 suppose that 16 data points in curve 88 comprise the wave delineated by the start point and end points, and neural network 3 required 10 data points. (As opposed to 50 required in the preferred embodiment) Thus, it is desired to translate curve 88 having 16 data points into curve 90 having only 10 data points. Since no collected data points exist, at the exact points of the desired time arrival (point x1 and x2 in FIG. 9) the amplitude for x1 is interpolated from A and B on curve 88 and the amplitude for x2 is interpolated from points C and D on curve 88.

Amplitude normalization techniques may be tailored to the specific pattern recognition paths employed by the present invention. In capnogram analysis, the capnogram's morphology is the primary determinant of capnogram classification. However, the only difference between an entirely normal capnogram and one produced as a result of an expiratory valve leak is the base line off-set of the wave. Therefore, the maximum amplitude of each wave is normalized so that all capnograms passed to neural network 3 have identical peak values. Importantly, the minimum values of each wave are preserved as a ratio of the maximum amplitude. This transformation is performed as illustrated in FIG. 10. In particular, wave 92 has a minimum value of wave amplitude b at point 94 and a maximum value wave amplitude of a at point 96. The amplitude of each data point is then scaled by 100/a. Thus, as illustrated in curve 98, the new wave maximum amplitude is 100 (a×100/a). The new wave minimum amplitude is equal to b×100/a.

Lead and lag normalization is performed to align morphologically similar segments of the capnogram in the input nodes of neural network 3. While neural network 3 could classify capnograms which are shifted earlier or later in the input layer, this translational variability reduces the classification accuracy and complicates training. If not for lead and lag normalization, capnogram alignment in the input node vector of neural network 3 would be dependant upon the performance of neural networks 1 and 2. Therefore, if neural networks 1 and 2 are performing well one would not expect significant variability in wave alignment. However, it is possible that neural networks 1 and 2 will need modification and that the modified networks will pick slightly different staring point and end points while neural network 3 remains fixed (not retrained). Thus, if all new starting points were slightly earlier and all new ending points slightly earlier, all new capnograms passed to neural network 3 would be shifted later in the input layer. As a result, neural network 3 might not still perform optimally. Therefore, by performing lead and lag normalization, we isolate the performance and training of neural networks 1 and 2 from the training of neural network 3. This greatly simplifies the task of training and permits refinements and customization of the system to be performed in a modular fashion where changes in one section do not require retraining or reconfiguration of another module.

Figure 12:
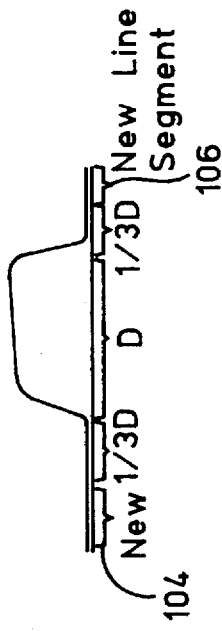
FIG. 12 is a diagram of the lead and lag normalization of a waveform in accordance with the present invention.
Figure 13:
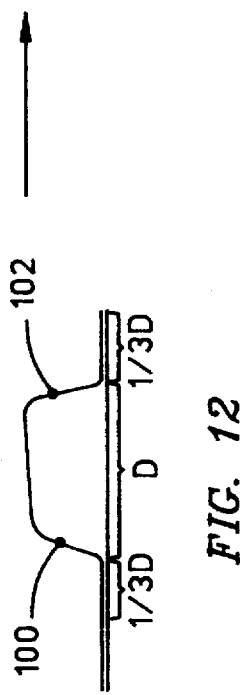
FIG. 13 is a diagram of addition details of the lead and lag normalization process.

Referring now to FIG. 12 lead and lag normalization is performed by locating the point of half-maximum capnogram amplitude on the rising and falling segments of the wave ($A_{1/2}$RISE100 and $A_{1/2}$FALL102), respectively) Next, the wave duration D between these two points is measured. Then, the amplitude of the wave at the points ⅓ earlier than $A_{1/2}$RISE100 and ⅓ D later than $A_{1/2}$FALL, are measured. Lines 104 and 106 are then extended from those points to produce new lead and lag segments as shown in FIG. 13.

Figure 14:
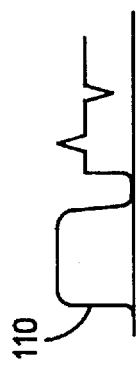
FIG. 14 is an example of a waveform from arterial pressure waves in accordance with an additional embodiment of the present invention.
Figure 15:
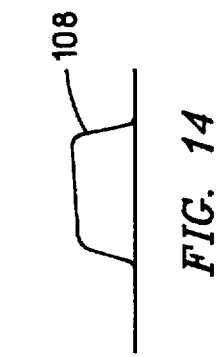
FIG. 15 is another diagram of lead and lag normalization performed on arterial pressure waves in accordance with an alternative embodiment of the present invention.

Waveforms other than capnograms may require different techniques for normalization. For example, arterial pressure wave should be normalized for maximum and minimum values but not for lead and lag segments. In this case, it might be desirable to append a first derivative of a waveform for input to for input to neural network number 3. Thus, where the raw waveform appears as shown in curve 108 of FIG. 14, the normalized waveform 110 is shown in FIG. 15 with the first derivative appended. This addition to the waveform is used for the purpose of improving Neural Network No. 3's ability to classify subtle feature differences.

Normalization is usually performed in the following order: (1) amplitude; (2) lead-leg; (3) time. The normalized waves are then fed directly to the 50 input nodes of neural network 3. Neural network 3, has been previously trained to recognize and classify the wave's morphology as for example, one of the wave classes shown in FIG. 2.

Figure 16:
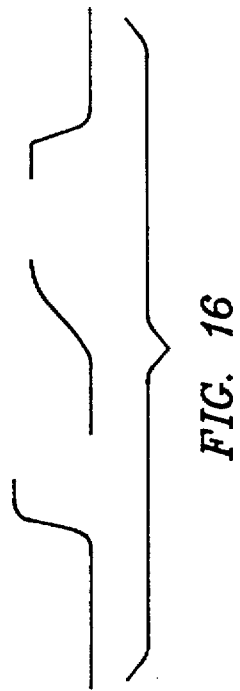
FIG. 16 illustrates several partial waves to be identified by the present invention.

Every output node of neural network 3 corresponds to a different classification. However, output node number 1 is different. It works in conjunction with neural networks 1 and 2 to validate the acquisition of an acceptable wave. Referring now to FIG. 16 partially collected waves, noise and other spurious data such as those shown in this figure are actively identified.

Referring now to FIG. 17 a table of six output nodes of neural network 3 in accordance with a preferred embodiment of the present invention is shown. It is seen that this network has been trained to recognize partial waves by producing an output in output exceeds some threshold (usually 0.3), no further analysis of the data is performed. Instead, additional data is collected and appended to the data already in the buffer and presented again to neural networks numbers 1 and 2. It is possible to append data because the buffer is not cleared until a valid wave is identified by neural network number 3. Thus, neural network number 3 performs two functions: One, validity checking of the captured (putative) wave. Two, preliminary classification of the waves morphology.

Referring now to FIG. 18, an example of a wave 110 is shown. The outputs of four of the output nodes of neural network number 3 are also shown. Each of the output nodes will have an output value which ranges from 0 to 1, representing a different classification. The greater the value associated with an output node, the more strongly the network believes this wave belongs to that class. In the case shown in FIG. 18 the partial wave node value of 0.1 indicates that the wave is not a partial wave. The normal value of 0.8 indicates that the wave 110 can be accepted as being normal and the output can then be transmitted to the display unit 54 for utilization by operating room personnel, or subsequent processing equipment.

In some cases, however, the outputs of neural network 3 will be in conflict (such as "normal" in combination with any class of abnormal), or when no obvious winner exists. In this case, further analysis of the data by neural network number 4, called the arbitration network, is used. The arbitration network number 4 analyzes the outputs of neural network number 3 in the context of other information about the wave.

For example, if the output of neural network number 3 is as shown in FIG. 19, in this case, it is not clearly a normal wave since the normal value is only 0.6 and the expiratory value is 0.5. A human expert analyzing wave 112 in FIG. 19 would possibly be able to recognize that the capnogram wave 112 is slightly above the baseline because the patient is breathing at a high respiratory rate. In this case the baseline elevation is due to monitor response time characteristics and not necessarily to a valve abnormality. The neural network number 3 is technically correct in identifying an expiratory valve defect because of the elevated baseline. Refer to curve 60 in FIG. 2. Furthermore, the neural network's confusion (normal and exp valve is understandable because the wave appears close to normal and the elevation is very slight.

To resolve this ambiguity neural network number 4 is supplied with the same information that permits the human expert to correctly classify the wave. Thus, neural network number 4 receives as inputs the outputs of neural network number 3 and additional data such as respiratory rate, peak and minimum $CO_2$ values. For example, neural network number 4 inputs may comprise the following: normal-0.6, cleft 0.1, expiratory valve defect 0.5, respiratory rate 26, peak $CO_2$ 6%, minimum $CO_2$ 0.5%. (The partial wave category used in neural network 3 is no longer needed for neural network number 4).

The outputs of five output nodes of neural network number 4 are shown in FIG. 20. In this example, neural network number 4 outputs may be as follows: normal 0.9, cleft 0.0, inspiratory valve 0.0, exp valve 0.1, unknown 0.0. During system development, when neural network number 3 classification is ambiguous, an expert can examine the outputs of neural network number 3 and use his expertise to train neural network number 4. Although in accordance with the preferred embodiment, neural network 4 is given additional contextual data, it is also possible to omit the additional data and simply train neural network number 4 to interpret patterns in neural network number 3's outputs to produce the correct outputs. Neural network number 4 like neural network number 3 is a three layer perceptron containing six to ten input nodes and five output nodes and may have between 4 and 8 hidden nodes of course these values may vary widely on the application.

Figure 21:
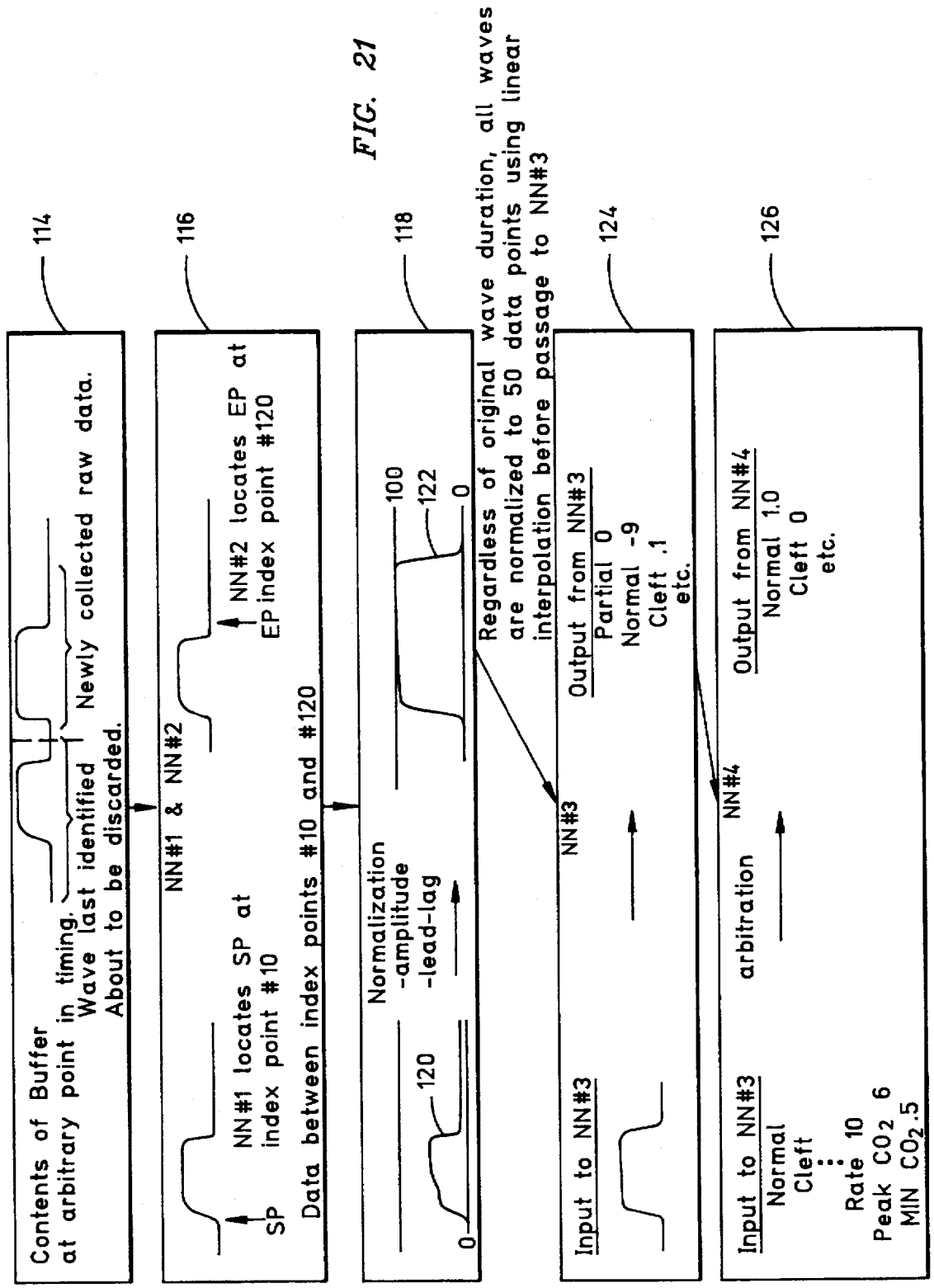
FIG. 21 is an overall diagram of the processes performed by the present invention in neural networks 1–4.

Referring now to FIG. 21, a summary of the steps performed by the waveform analysis system 30 are shown. In the first step 114 the entire contents of the buffer 40 at an arbitrary point in time is shown. To the left of the vertical dotted line the wave which was last identified is shown and is about to be discarded from the buffer. To the right of the vertical dotted line is the newly collected raw data which is to be transmitted to the inputs of neural networks number 1 and number 2.

In step 116 neural network number 1 locates a starting point SP at index point 10 in the buffer, (which corresponds to the tenth input node of neural network number 1). Likewise, neural network number 2 locates the end point EP at index point 120 in the buffer corresponding to the index node number 120. Data between index points 10 and 120 are then normalized in step 118. This normalization as discussed above includes time normalization, amplitude normalization and lead and lag normalization. Thus, the incoming curve 120 is transformed into the normalized curve 122. Regardless of the original wave duration, all the waves are normalized to 50 data points as discussed above before transmitting to the 50 input nodes of neural network number 3 in step 124. Neural network number 3 then produces output signals in its output nodes which classify the incoming wave. Should an ambiguity exist in this classification the information from neural network number 3 is transmitted to neural network number 4 in step 126 along with additional information such as respiratory rate, peak $CO_2$ and minimum $CO_2$. Neural network number 4 outputs then remove the ambiguity and correctly identify the wave as normal.

Training the neural networks 1–4 may be performed using training data devised from actual patient data or using data generated using an artificial lung attached to the breathing apparatus and capnogram monitor 24. Training in the preferred embodiment was in accordance with the back propagation procedure which is fully explained in the Ward System Group NeuroShell Manual published by Ward's Systems Group of Frederick, Md. and incorporated herein by reference. Neural networks 1–4 each required tens of thousands training cycles to train. The number of training cycles can vary widely depending on the application and the criteria for acceptable results. Using the NeuroShell hardware training board this was accomplished in approximately 8 hours. It will be appreciated that other neural network architectures besides back prop may also be successfully employed utilizing the techniques of the present invention.

The output of neural network number 4 may be used in a number of ways. For example, display 50 may simply display the classification indicated by neural network number 4 output, or may also include an alarm to alert operating room personnel to an abnormal condition. Further, display 50 may be coupled to other processing systems. For example, the display 50 may be coupled to an interactive system which permits the user to receive explanations of the detected abnormalities and to also receive instructions as to corrective measures which should be taken. Besides the operating room application, the waveform analysis system 30 of the present invention may be used as an intelligent input into a comprehensive patient monitoring system. Also this system design could be applied to many signals acquired simultaneously from one patient to perform intelligent diagnostics.

From the foregoing, it can be seen that the present invention provides a waveform analysis system that is capable of analyzing physiologic as well as non-physiologic waveforms and effectively segmenting the waveform, classifying the waveform and resolving ambiguities in classifications. This system avoids costly algorithm development, works rapidly enough for real-time deployment, and can be implemented at a reasonable cost. Furthermore, the modular construction of the waveform analysis system 30 in accordance with the present invention permits individual neural networks to be retrained and modified independently of the others. Furthermore, once the neural networks 1–4 are trained to a satisfactory degree, the internal synaptic weights derived by training may be set to fixed values and embodied in fixed weight hardware for inexpensive mass production. Those skilled in the art can appreciate that other advantages can be obtained from the use of this invention and that modification may be made without departing from the true spirit of the invention after studying the specification, drawings and following claims.

What is claimed is:

1. A method of analyzing a waveform in a signal using a neural network having input nodes and output nodes, said method comprising the steps of:

transmitting a first portion of said waveform to said neural network, such that N consecutive samples of said waveform are transmitted to N input nodes of said neural network;

said neural network being trained to recognize the starting point and ending point of said waveform by producing outputs which are a representation of an index number of the portion of the sample of the waveform corresponding to the starting and ending points; and classifying said waveform as one characteristic waveform type of a plurality of characteristic waveform types, or as an incomplete waveform, in response to the index number.

2. A method of analyzing a waveform in a signal, said signal having a plurality of characteristic waveform types, said method comprising the steps of:

providing a pretrained neural network having N input nodes and R output nodes, said neural network being trained to produce output signals in said output nodes which represent a plurality of classifications of said characteristic waveform types, one of said classifications indicating a partial waveform signifying that a complete waveform has not been received by said neural network; and transmitting said waveform to said N input nodes of said pretrained neural network, wherein said pretrained neural network produces an output which classifies said waveform as either a partial waveform or as one of said characteristic waveform types.

3. The method of claim 2 further comprising the steps of:

identifying the starting and end points of said waveform before the step of transmitting; and normalizing said waveform to comprise a predetermined duration and amplitude, wherein said starting and ending points of said waveform comprise N samples.

4. The method of claim 3 further comprising the step of normalizing the lead and lag portions of said waveform preceding said starting point and following said end point respectively.

5. A method of analyzing a waveform having a characteristic shape in a signal using a neural network, said method comprising the steps of:

using a classification means to classify said waveform based on its shape, said classification means assigning numerical values to the likelihood that said waveform belongs to one of a plurality of predetermined classes;

when said numerical values do not unambiguously indicate a single class, transmitting said numerical values to input nodes of a neural network;

transmitting additional information relating to said waveform to additional input nodes of said neural network; and said neural network being previously trained to classify said waveform by producing output numerical values representing the likelihood that said waveform belongs to one of a plurality of classes, said neural network being trained with inputs containing said additional information, said additional information serving to resolve said ambiguities between various classifications of waveform shapes by correlating an atypical shape of a particular waveform classification with particular values for said additional information.

6. The method of claim 5 wherein said waveform is a signal derived from a capnogram waveform and said classes produced by said classification means represent abnormalities in said capnogram waveform and said additional information transmitted to said neural network includes minimum $CO_2$, maximum $CO_2$ and respiratory rate.

7. A method for analyzing a waveform in a signal using neural networks having input nodes and output nodes, said method comprising:

transmitting a first portion of said waveform to first and second neural networks, such that N consecutive samples of said waveform are transmitted to N input nodes of said first and second neural networks;

said first and second neural networks being trained to recognize the starting point and ending point of said waveform by producing outputs which are a representation of an index number of the portion of the sample of the waveform corresponding to the starting and ending points;

providing a third neural network having N input nodes and R output nodes, said third neural network being trained to produce output signals at said output nodes which represent a plurality of classifications of respiratory waveform types, and one of said classifications indicating a partial waveforms signifying that a complete waveform has not been received by said third neural network;

transmitting said waveform to said N input nodes of said third neural network, wherein said third neural network produces an output which classifies said waveform as either a partial waveform or as one class of said respiratory waveform types;

when said numerical values do not unambiguously indicate a single class, transmitting said waveform to input nodes of a fourth neural network;

transmitting additional information relating to said waveform to additional input nodes of said fourth neural network; and said fourth neural network being previously trained to classify said waveform by producing output numerical values representing the likelihood that said waveform belongs to one of a plurality of classes, said fourth neural network being trained with inputs containing said additional information, said additional information serving to resolve said ambiguities between various classifications of said respiratory waveform types, by correlating an atypical waveform shape of a particular classification with particular values for additional information.

8. A system for analyzing a waveform in a signal using a neural network having input nodes and output nodes, said system comprising:

a neural network trained to recognize the starting point and ending point of said waveform by producing outputs which are a representation of an index number of the portion of the sample of the waveform corresponding to the starting and ending points;

means for transmitting a first portion of said signal to said neural network, such that N consecutive samples of said waveform are transmitted to N input nodes of said neural network; and means for classifying said waveform as one characteristic waveform type of a plurality of characteristic waveform types, or as an incomplete waveform in response to the N consecutive samples.

9. System for analyzing a waveform in a signal, said signal having a plurality of characteristic waveform types, said system comprising:

a pretrained neural network having N input nodes and R output nodes, said neural network being trained to produce output signals in said output nodes which represent a plurality of classifications of characteristic waveform types, one of said classifications indicating a partial waveform signifying that a complete waveform has not been received by said neural network; and means for transmitting each of said neural network samples to one of said N input nodes of said pretrained neural network, wherein said pretrained neural network produces an output which classifies said waveform as either a partial waveform or as one of said characteristic waveform types.

10. The system of claim 9, further comprising:

means for identifying the starting and end points of said waveform; and means for normalizing said waveform to comprise a predetermined duration and amplitude, wherein said starting and ending points of said waveform comprise N samples.

11. The system of claim 10 further comprising means for normalizing the lead and lag portions of said waveform preceding said starting point and following said end point respectively.

12. A system for analyzing a waveform having a characteristic shape in a signal using a neural network, said system comprising:

a classification means for classifying said waveform based on its shape, said classification means assigning numerical values to the likelihood that said waveform belongs to one of a plurality of predetermined classes;

means for transmitting said numerical values to input nodes of a neural network when said numerical values do not unambiguously indicate a single class;

means for providing additional information relating to said waveform to additional input nodes of said neural network; and wherein said neural network being previously trained to classify said waveform by producing output numerical values representing a likelihood that said waveform belongs to one of a plurality of classes, said neural network being trained with inputs containing said additional information, said additional information serving to resolve said ambiguities between various classifications of waveform shapes by correlating an atypical shape of a particular waveform classification with particular values for said additional information.

13. The method of claim 12 wherein said waveform is a signal derived from a capnogram waveform, said classes produced by said classification system represent abnormalities in said capnogram waveform, and said additional information transmitted to said neural network includes minimum $CO_2$, maximum $CO_2$ and respiratory rate.

* * * * *